US008447092B2

(12) United States Patent
Kii et al.

(10) Patent No.: US 8,447,092 B2
(45) Date of Patent: May 21, 2013

(54) OBSERVATION DEVICE FOR OBSERVING CELLS OR THE LIKE

(75) Inventors: Hiroaki Kii, Kanasak (JP); Yasujiro Kiyota, Tokyo (JP)

(73) Assignee: Nikon Corporation, Tokyo (JP)

( * ) Notice: Subject to any disclaimer, the term of this patent is extended or adjusted under 35 U.S.C. 154(b) by 819 days.

(21) Appl. No.: 12/292,623

(22) Filed: Nov. 21, 2008

(65) Prior Publication Data

US 2009/0087075 A1  Apr. 2, 2009

Related U.S. Application Data

(63) Continuation of application No. PCT/JP2007/060465, filed on May 22, 2007.

(30) Foreign Application Priority Data

May 22, 2006  (JP) .................................. 2006-141677

(51) Int. Cl.
    *G06K 9/00* (2006.01)
(52) U.S. Cl.
    USPC ......................................................... 382/133
(58) Field of Classification Search
    None
    See application file for complete search history.

(56) References Cited

U.S. PATENT DOCUMENTS

| 4,197,088 | A * | 4/1980 | Meserol et al. ............... 436/528 |
| 4,400,353 | A * | 8/1983 | Meserol et al. ................. 422/73 |
| 4,806,776 | A * | 2/1989 | Kley ....................... 250/559.24 |
| 6,381,353 | B1 * | 4/2002 | Weiss ............................ 382/133 |
| 7,126,120 | B2 * | 10/2006 | Inada ............................ 250/307 |
| 7,567,726 | B2 * | 7/2009 | Westphal ....................... 382/274 |
| 7,848,552 | B2 * | 12/2010 | Schutze et al. ................. 382/128 |
| 2006/0098895 | A1 | 5/2006 | Westphal |
| 2007/0058164 | A1 * | 3/2007 | Shibata et al. ............. 356/237.2 |
| 2007/0160280 | A1 * | 7/2007 | Schutze et al. ................. 382/133 |
| 2008/0032325 | A1 * | 2/2008 | DiMarzio et al. ............... 435/29 |
| 2009/0087075 | A1 * | 4/2009 | Kii et al. ....................... 382/133 |

FOREIGN PATENT DOCUMENTS

| JP | A-62-050607 | 3/1987 |
| JP | A-06-303965 | 1/1994 |
| JP | A-06-028453 | 2/1994 |
| JP | A-06-508021 | 9/1994 |
| JP | A-10-024283 | 1/1998 |

(Continued)

OTHER PUBLICATIONS

Sep. 20, 2011 Search Report issued in European Patent Application No. 07743899.2.
Oct. 25, 2011 Office Action issued in Japanese Patent Application No. 2006-141677 (with partial English Translation).

(Continued)

*Primary Examiner* — Bhavesh Mehta
*Assistant Examiner* — Tahmina Ansari
(74) *Attorney, Agent, or Firm* — Oliff & Berridge, PLC

(57) ABSTRACT

An observation device that observes a test specimen such as cultured cells or the like includes: an illumination device that illuminates the test specimen; an image-capturing device that acquires an image of the test specimen illuminated by the illumination device; a storage unit that stores correlation data manifesting a correlation relationship between an occupation ratio of the test specimen within a culture vessel, and statistically processed data regarding to luminance information of the test specimen; and a calculation unit that obtains the statistically processed data based upon luminance information in a specified color of the test specimen captured by the image-capturing device, and calculates the occupation ratio of the test specimen within the culture vessel using the correlation data in the storage unit.

12 Claims, 13 Drawing Sheets

FOREIGN PATENT DOCUMENTS

| | | |
|---|---|---|
| JP | A-2001-340072 | 12/2001 |
| JP | A-2003-135095 | 5/2003 |
| JP | A-2004-016194 | 1/2004 |
| WO | WO 92/16614 | 10/1992 |
| WO | WO/2005114135 | * 12/2005 |

OTHER PUBLICATIONS

"Saikingaku Jishu Teiyo." Edited by The Institute of Medical Science, The University of Tokyo. 5th Revised Edition. Maruzen Co., Ltd. p. 109. (with translation).

* cited by examiner

|  | BASIC FREQUENCY (32.1/MM) | BASIC FREQUENCY × 2 (64.3/MM) | BASIC FREQUENCY × 3 (96.5/MM) |
|---|---|---|---|
| 1) MTF (CULTURE MEDIUM ONLY) | 0.284 | 0.0128 | 0.0201 |
| 2) MTF (CELLS) | 0.189 | 0.00618 | 0.0105 |
| PROPORTION OF 2) WITH RESPECT TO 1) | 66.4 | 48.1 | 52.6 |

OBSERVATION DEVICE FOR OBSERVING CELLS OR THE LIKE

This application is a continuation of International Application No. PCT/JP 2007/060465 filed May 22, 2007.

INCORPORATION BY REFERENCE

The disclosures of the following applications are herein incorporated by reference:
Japanese Patent Application No. 2006-141677 filed May 22, 2006 International Application No. PCT/JP 2007/060465 filed May 22, 2007

BACKGROUND OF INVENTION

1. Field of the Invention

The present invention relates to an observation device for observing cells.

2. Description of Related Art

The following type of cell culture device is known from Japanese Laid-Open Patent Publication 2004-16194. According to this cell culture device, an image regarding to the inside of a cell culture vessel that has been photographed with a camera is analyzed, and the cell area and the number of cells in the cell vessel are detected.

SUMMARY OF THE INVENTION

However, while, no technique for detecting the cell area and the number of cells in the cell vessel is disclosed in cell culture devices of prior art, generally, in order to detect these, it is necessary to photograph a phase difference image of the cells and to analyze this phase difference image. Due to this, a phase difference microscope for acquiring this phase difference image is required, and the problem arises that this device is expensive.

An observation device that observes a test specimen such as cultured cells or the like, includes: an illumination device that illuminates the test specimen; an image-capturing device that acquires an image of the test specimen illuminated by the illumination device; a storage unit that stores correlation data manifesting a correlation relationship between an occupation ratio of the test specimen within a culture vessel, and statistically processed data regarding to luminance information of the test specimen; and a calculation unit that obtains the statistically processed data based upon luminance information in a specified color of the test specimen captured by the image-capturing device, and calculates the occupation ratio of the test specimen within the culture vessel using the correlation data in the storage unit.

It is preferred that this observation device further includes a shift unit that shifts an illumination light from the illumination device over the test specimen, and wherein the calculation unit calculates the occupation ratio of the test specimen within the culture vessel based upon two or more images that are acquired while shifting the illumination light with the shift unit.

The observation device described above, wherein: the illumination device illuminates the culture vessel with a planar light source consisting of bright portions and dark portions repeated, so that dark field regions are formed in the image acquired by the image-capturing device. In this case, it is preferred that the observation device further includes a shift unit that shifts an illumination light from the illumination device over the test specimen, and wherein the calculation unit calculates the occupation ratio of the test specimen within the culture vessel, based upon two or more images that are acquired while shifting the illumination light with the shift unit.

In this observation device, the image-capturing device includes a plurality of pixels that each output a resolved RGB color signal having information for a plurality of colors; a single pixel data in the image data is generated based upon the plurality of resolved RGB color signals; and the shift unit can shift the illumination device so as to eliminate an image in a grey colored region that is formed at a boundary of a dark field region upon the image acquired by the image-capturing device, the image in the grey colored region being acquired as an image in the dark field region.

The calculation unit of the observation device in the present invention extracts an image of the dark field region from the image acquired by the image-capturing device, and calculates the occupation ratio of the test specimen within the culture vessel based upon luminance information in the specified color of the test specimen in the image in the dark field region that has been extracted.

In the observation device according to the present invention, the calculation unit can calculate the occupation ratio of the test specimen within the culture vessel by referring to the correlation data in the storage unit while using the statistically processed data based upon luminance information in the specified color of the test specimen in the image of the dark field region. It is preferred that the statistically processed data is a variance and a kurtosis of a histogram that is generated based upon the luminance information in the specified color.

An observation device that observes a test specimen such as cultured cells or the like, according to another aspect of the present invention, includes an illumination device that illuminates the test specimen; an image-capturing device that acquires an image of the test specimen illuminated by the illumination device; a storage unit that stores correlation data manifesting a correlation relationship between an occupation ratio of the test specimen within a culture vessel and statistically processed data of spatial frequency information of the test specimen; and a calculation unit that obtains the statistically processed data based upon the spatial frequency information of the test specimen captured by the image-capturing device, and calculates the occupation ratio of the test specimen within the culture vessel using the correlation data in the storage unit.

This observation device further includes: a shift unit that shifts an illumination light from the illumination device over the test specimen in a rotational direction, and wherein: the calculation unit can calculate the occupation ratio of the test specimen within the culture vessel based upon two or more images that are acquired while shifting the illumination light with the shift unit.

Furthermore, in the observation device according to the present invention, the calculation unit can calculate the spatial frequency information from luminance information in a specific color of the test specimen in the image acquired via image capture by the image-capturing device. It is preferred that the statistically processed data of the spatial frequency information is a proportion of the spatial frequency information of an image when the test specimen is occupying the interior of the culture vessel, with respect to the spatial frequency information of an image when no test specimen is occupying the interior of the culture vessel.

BRIEF DESCRIPTION OF THE DRAWINGS

FIG. 1A shows the structure of the observation device schematically, and FIG. 1B shows the concept of the optical system section of the observation device;

DESCRIPTION OF PREFERRED EMBODIMENTS

Embodiment One

Figure 1A:
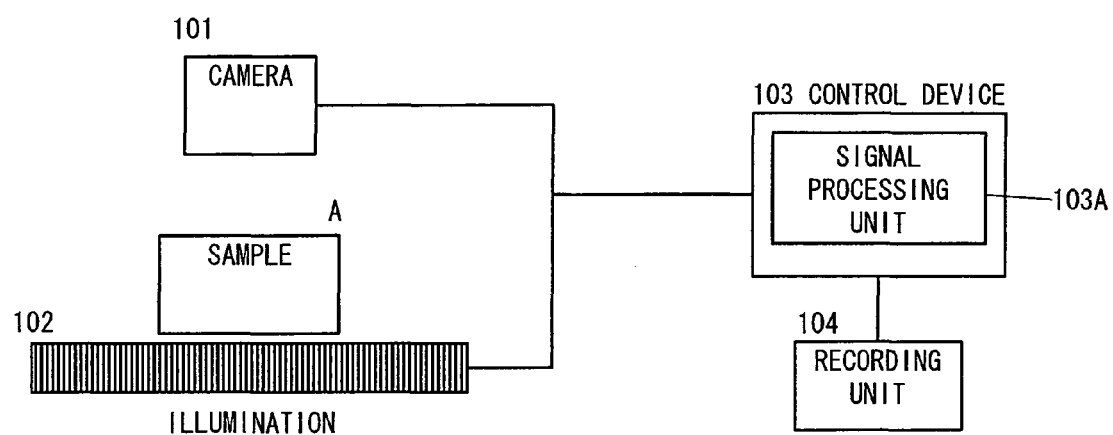
FIGS. 1A and 1B are figures showing the structure of an embodiment of an observation device.
Figure 1B:
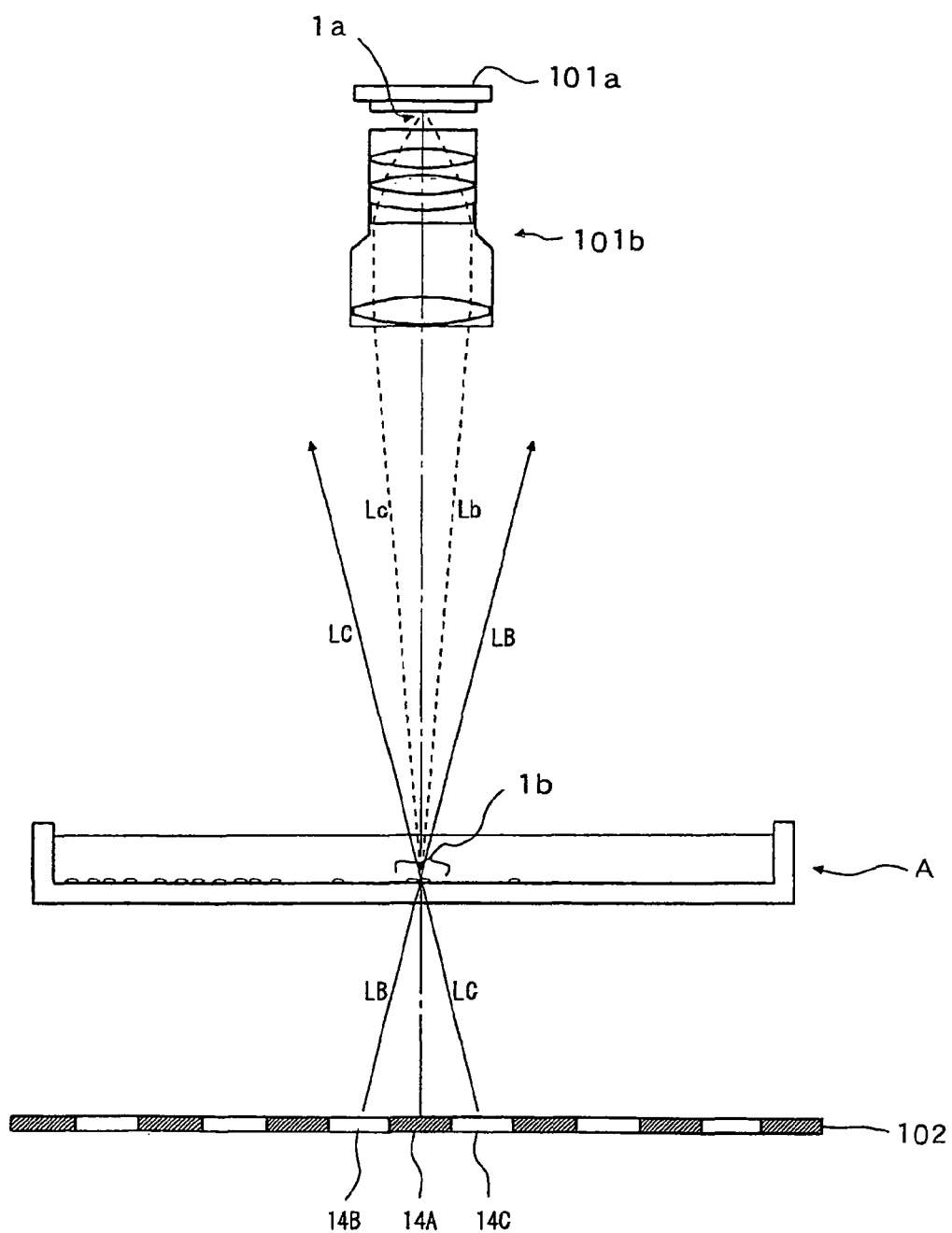

FIGS. 1A and 1B are figures schematically showing the structure of an embodiment of an observation device according to the first embodiment. The observation device 100 includes a camera 101, an illumination device 102, a control device 103, and a recording unit 104. With this observation device 100, illumination light is irradiated by the illumination device 102 from underneath towards a sample A that is the subject for observation, and an image of the light that passes through the sample A at this time is captured by the camera 101. It should be understood that the sample A is a test specimen of cells or the like cultured in, for example, a culture vessel.

The control device 103 processes an image acquired by the camera 101 and calculates the occupation ratio of the cells in the culture vessel. In other words, an example will be explained in which the occupation ratio of the cells is calculated with respect to the entire area of the culture medium covering the entire bottom surface of the culture vessel. The concrete details of the processing performed by the control device 103 will be described hereinafter.

The camera 101 is, for example, a color CCD camera, and is installed so as to be able to photograph the entire interior of the culture vessels from above the sample A. Furthermore, the camera 101 includes an imaging optical system, and the light emitted from the sample A is captured by this imaging optical system and an image is formed upon an image photography surface of an image sensor.

Figure 2:
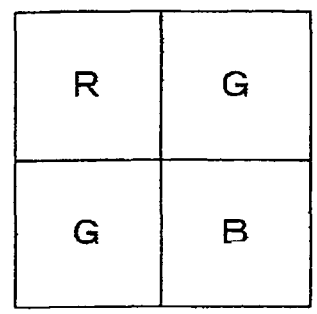
FIG. 2 is a figure showing a color filter matrix of a CCD of a camera 101.

The image data that has been obtained by image captured with this camera 101 is expressed in the RGB color system. And it will be supposed that color information for each RGB color component exists for every one of the pixels that make up this image data. For example, if the matrix color filter shown in FIG. 2 is provided over the entire extent of the light reception surface of the CCD included in the camera 101, the control device 103 may perform interpolation processing upon the image data outputted from the CCD, and convert it so that color information for each RGB color component exists for each pixel. The camera 101 captures an image of the sample A based upon a command from the control device 103, and outputs the captured image data to the control device 103, and the control device 103 records this image data upon the recording unit 104.

The illumination device 102 is installed so as to irradiate the sample A from its underneath. Due to this, the camera 101 is able to capture an image of the light transmitted through the sample A that is illuminated by the illumination device 102. The illumination device 102 includes a light source not shown in the figures and a slit plate having a sequence of areas that allow light to pass and areas that block light in the form of bands at the constant intervals, and illuminates the sample A as a planar light source consisting of repeated bright portions and dark portions. In other words, the illumination device 102 irradiates light upon the sample A in stripe form (stripe light), consisting of ranges in which direct light is illuminated thereupon and ranges in which light is intercepted therefrom. It should be understood that, instead of using a slit plate, it would also be acceptable, for example, to provide this stripe light with a liquid crystal display or the like. Moreover, in this specification, the constant interval at which the areas that allow light to pass and the areas that block light are repeated in the form of bands upon the slit plate described above, will be termed the slit interval.

At this time, it is arranged for white regions that correspond to the areas where direct light is irradiated upon the image acquired by the camera 101, and black regions (dark field of view regions) that correspond to the areas where the light has been intercepted to be formed by the repetition of the bright portions and the dark portions in the sample light that is irradiated from the illumination device 102.

Moreover, the illumination device 102 is installed so as to be shiftable in the perpendicular direction with respect to the direction of irradiation of the stripe light, in other words so as to be shiftable in the left and right direction in FIG. 1A, so that it can shift the irradiation position of the stripe light with respect to the sample A. For example, for a range upon the sample A upon which direct light is being irradiated, the illumination device 102 can be shifted so as to intercept direct light therefrom. It should be understood that the irradiation of stripe light by the illumination device 102 and the shifting of the illumination device 102 are controlled by the control device 103.

Now, using FIG. 1B, the operation of the optical system of the observation device 100 will be explained. It should be understood that FIG. 1B is a figure showing the concept of the optical system of the observation device 100. First, the explanation will concentrate upon a dark portion 14A upon the planar light source and a partial region 1b upon the sample A that is directly above this dark portion 14A. Although the rays LB and LC from the two bright portions 14B and 14C adjacent to the dark portion 14A are incident upon this partial region 1b, no light is incident thereupon from the dark portion 14A. Accordingly, this partial region 1b is illuminated obliquely by the rays LB and LC.

Although portions of the rays LB and LC that are incident upon this partial region 1b pass through it just as they are without being diffracted thereby, other portions of the rays LB and LC are affected by the influence of the difference of refractive index in the partial region 1b, and a rediffracted (or scattered). The non-diffracted rays LB and LC that have passed through this partial region 1b without alteration are not incident upon the pupil of the imaging optical system 101b that the camera 101 possesses, but the portion consisting of the diffracted (or scattered) rays Lb and Lc created by the partial region 1b is incident upon the pupil of the imaging optical system 101b.

At this time, in the region 1a upon the image sensor 101a that is in a conjugate relationship with the partial region 1b, an image of the dark portion 14A and an image of the contour of a phase object present in the partial region 1b are formed as mutually superimposed. In other words, a dark field image of the partial region 1b is formed. Here, when seen from the partial region 1b, the angle subtended by the two bright portions 14B and 14C is sufficiently small. Accordingly, the angle of illumination of the partial region 1b by the rays LB and LC is also sufficiently small. At this time, the observed image of the partial region 1b comes to be generated by the diffraction light bands Lb and Lc of high intensity that are emitted at small angles. Due to this, the brightness of the partial region 1b also becomes sufficiently high.

Moreover, the above fact also applies for each of the regions upon the sample A that are directly above the dark portions. Accordingly, the image that is acquired by the image sensor 101a is a striped image consisting of white regions and black regions, as described above.

The control device 103 includes a CPU, memory, and other peripheral circuitry, and is functionally provided with a signal processing unit 103a. And the control device 103 irradiates the entire culture vessel with stripe light under the control of the illumination device 102, and simultaneously controls the camera 101 so as to capture and image of the stripe light that has passed through the culture vessel. And the signal processing unit 103a executes image processing upon the image that has been obtained by capturing image with the camera 101, and extracts only an image that corresponds to the interior of the culture vessel as a stripe image from this image.

Due to this, the signal processing unit 103a extracts the edges from the image by, for example, performing a known type of edge extraction processing, and detects edges that make up a shape that agrees with the shape of the culture vessel, among the extracted edges. And it recognizes the interior thereof as being the interior of the culture vessel, and extracts the stripe image. Due to this, a stripe image is obtained, as for example shown in FIG. 3. It should be understood that although, in the example of FIG. 3, a case is shown in which the edges of a quadrilateral are extracted as the shape of the culture vessel, a circular shaped stripe image would be extracted in the case of a circular culture vessel.

In this stripe image, the areas where direct light has impinged after passing through the slit plate are captured as the white regions 3a in the image, while the areas where the light is intercepted are captured as the black regions 3b (the dark field region) in the image. At this time since, as described above, color information for each of the RGB color components is present for each pixel in the image data for this stripe image, accordingly, when the boundary (the region of diffracted light) between an area where direct light passes through and an area where the light is intercepted is included upon 1 pixel×1 line, the pixels that correspond to this boundary come to be photographed as gray regions (regions of diffracted light). Due to this, in the stripe image, gray regions (gray zones) 3c appear on the boundaries between the white regions 3a and the black regions 3b.

Based upon the stripe image that has been acquired by the camera 101 in this manner, the signal processing unit 103a calculates the occupation ratio of the cells within the culture vessel (i.e. the cell occupation ratio). In other words, if it is supposed that, as described above, a culture medium is present so as to fill over the bottom surface of the culture vessel, the occupation ratio of the cells with respect to the entire culture medium upon the bottom surface of the culture vessel is calculated. In the following, the theory of this calculation of the cell occupation ratio in the first embodiment will be explained.

Figure 4:
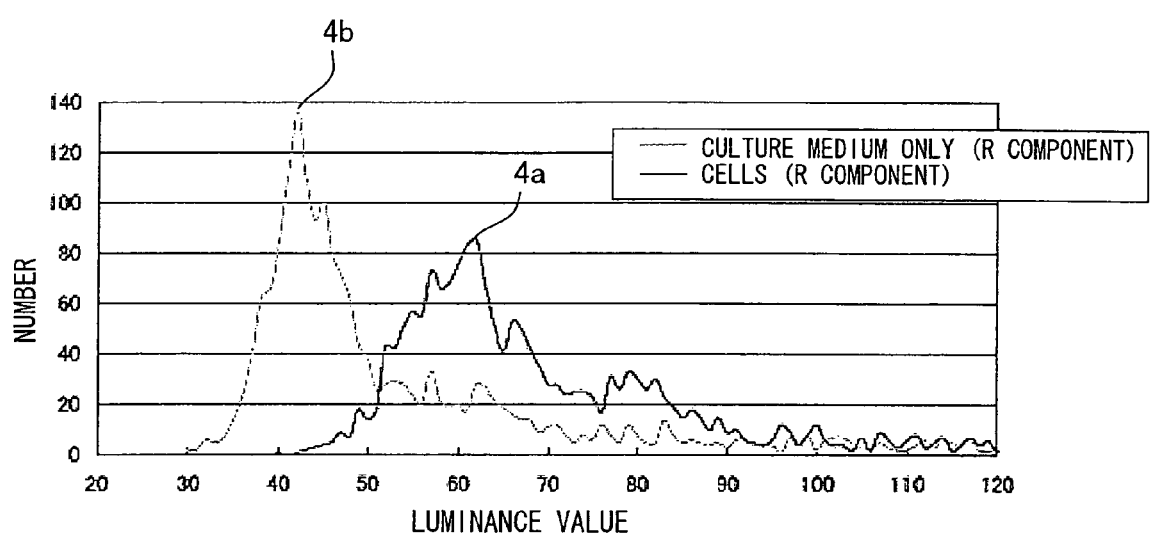
FIG. 4 is a figure showing a concrete example of a histogram of number of pixels against luminance value, for an R component.

For both an image (the culture medium image) that has been acquired by capturing an image of only a culture medium in which no cells are present, and also an image that has been acquired by capturing an image of a culture medium in which cells are present (the cell/culture medium image), the luminance values of the black regions 3b in each R, G, and B color component are acquired, and when a histogram of the number of pixels with respect to the luminance value is generated for, for example, the R color component, the result is as shown in FIG. 4.

As shown in this FIG. 4, the shapes of the histograms of the culture medium image and the cell/culture medium image are different, due to the difference in the refractive indexes for the stripe light. In concrete terms, at the peak position 4a of the histogram for the cell/culture medium image, the shape of the histogram is smoother than at the peak position 4b of the histogram for the culture region. This type of discrepancy of shapes depends upon the presence or absence of cells. It should be understood that although, in FIG. 4, histograms of the number of pixels with respect to the luminance value for the R component are shown for a culture medium image and a cell/culture medium image, similar results would also be obtained for the other color components.

Figure 5:
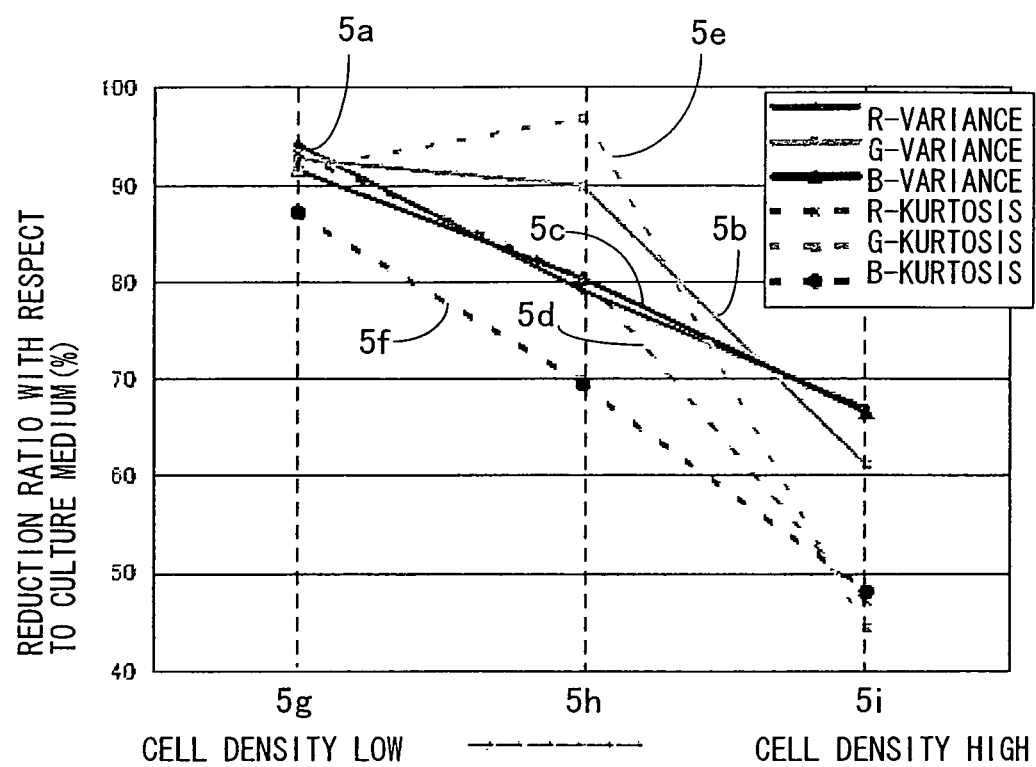
FIG. 5 is a figure showing, for each color component and cell density, the relationship between the variance and the kurtosis of histograms of a culture medium image and a cell/culture medium image.

In this embodiment, a graph like the one shown in FIG. 5 is obtained by paying close attention to this type of difference between the shape of the histogram for the culture medium image and the shape of the histogram for the cell/culture medium, and taking the density of cells in the culture vessel as a parameter when the variance and the kurtosis of the histograms for the culture medium image and the cell/culture medium image are obtained for each color component. This graph shown in FIG. 5 shows a concrete example in a case constructed by calculation upon data 5g obtained when the proportion of cells with respect to the culture medium (i.e. the cell density) was made to be about 20%, upon data 5h when it was made to be about 50%, and upon data 5i when it was made to be about 100%.

As shown in FIG. 5, for all of the variance 5a of the histogram for the R component (the R component variance), the variance 5b for the G component, the variance 5c for the B component, the kurtosis 5d of the histogram for the R component, the kurtosis 5e for the G component, and the kurtosis 5f for the B component, when the occupation ratio of the cells is large (100%), the variance and the kurtosis of the histogram become smaller than when the occupation ratio of the cells is small (20%). In particular, for the R component and the B component, the kurtosis and the variance of the histograms decrease along with increase of the occupation ratio of the cells.

It should be understood that, in the example shown in FIG. 5, the case is shown in which transparent cells are cultured by using, for example, a red colored culture medium in the culture vessel; and, due to this, the result is obtained that the kurtosis and the variance of the histograms for the R component and the B component decrease along with increase of the occupation ratio of the cells. However, if the type of the cells or the color of the culture medium is different, sometimes the color component(s) for which the kurtosis and the variance of the histogram(s) decrease along with increase of the occupation ratio of the cells may be different.

In this embodiment, by paying close attention to the color component(s) for which the kurtosis and the variance of the histogram(s) decrease along with increase of the occupation ratio of the cells, the occupation ratio of the cells with respect to the culture medium is calculated from the kurtosis and the variance of the histogram(s) for this color component(s). In other words, if for example the color of the culture medium is red, the signal processing unit 103a constructs the histogram for the R component shown in FIG. 4, and calculates the kurtosis and the variance of this histogram. And, based upon the graph shown in FIG. 5 that is obtained in advance by experiment, the signal processing unit 103a calculates the occupation ratio of the cells for the kurtosis and the variance of the histogram that have been calculated.

It should be understood that since, as described above, the graphs shown in FIG. 5 exhibit different tendencies according to the type of the cells and the color of the culture medium, provided that experimental data has been obtained in advance for each type of cells and each color of culture medium that may be expected, it becomes possible to calculate the occupation ratio of the cells according to the conditions.

In concrete terms, the signal processing unit 103a calculates the occupation ratio of the cells with respect to the culture medium by processing the image data in the following manner. First, the control device 103 controls the illumination device 102, as described above, so as to irradiate stripe light upon the sample A, in other words upon the culture vessel. And then the control device 103 controls the camera 101 to capture an image of the light that passes through the culture vessel, and records the image data that it has obtained upon the recording unit 104. Thereafter, the control device 103 shifts the illumination device 102.

In other words, as described above, by contrast to the fact that it is necessary for the signal processing unit 103a to obtain the occupation ratio of the cells based upon a histogram for the black regions 3b upon the stripe image, the stripe image includes both the white regions 3a and the gray zones 3c. Due to this, if the occupation ratio of the cells is calculated by extracting only one black region 3b from the stripe image, then it is not possible to calculate the occupation ratio of the cells in the white regions 3a and the gray regions 3c, so that there is a possibility that it may not be possible to obtain an accurate calculation result.

In order to calculate the occupation ratio of the cells from the entire interior of the culture vessel, the control device 103 acquires a plurality of images while shifting the illumination device 102, in other words the stripe light, to the left and right in FIG. 1B, in the following manner. The shift amount for the stripe light in one shift episode is determined as follows. It is arranged for the gray regions 3c and the black regions 3b in the first stripe image that has been obtained to overlap, and moreover for the black regions 3b in this first obtained stripe image and the black regions 3b in the newly obtained image, to overlap by at least width of one pixel. And the illumination device 102 is shifted by just the shift amount that is determined in this manner, the camera 101 is controlled to acquire a stripe image, and the image data that has been acquired is recorded upon the recording unit 104.

This processing is repeated a predetermined number of times, until the white regions 3a and the gray zones 3c upon the stripe image that is first obtained at the first processing disappear. In other words, a plurality of image data are acquired while shifting the illumination device 102. Based upon this plurality of image data, it becomes possible to calculate the cell occupation ratio over the entire culture vessel. It should be understood that, since how many times the illumination device 102 is to be shifted and how many times image capture by the camera 101 is to be performed vary according to the slit interval, it is necessary to set the number of times for processing in advance corresponding to the slit interval.

The signal processing unit 103a reads in from the recording unit 104 the stripe images that have been captured in this manner, extracts the black regions 3b from within these stripe images, and sets a calculation subject region 3d (refer to FIG. 3) of a predetermined size within each of the black regions 3b that have thus been extracted. Due to this, it is possible to eliminate the gray zones 3c and set calculation subject regions 3d that consist only of black regions. It should be understood that although, by way of example, in the above it has been explained that regions of a predetermined size within the black regions 3b are set as the calculation subject regions 3d, it would also be acceptable to arrange to set the entire black regions 3b as the calculation subject regions.

And statistical processing is performed upon each of the calculation subject regions 3d. In other words, for each of the calculation subject regions 3d that has been set, a histogram of number of pixels for luminance value is constructed for each of the R, G, and B color components, and the variance and kurtosis of these histograms that have been constructed are obtained. And the signal processing unit 103a fits these values to the graphs shown in FIG. 5, that have been calculated in advance based upon experimental data and that indicates the relationship between the variance and kurtosis of the histograms and the occupation ratio of the cells, and thereby calculates the occupation ratio of the cells in each calculation subject region 3d. In other words, it compares together the kurtosis and the variance of the histograms that have been calculated, and the correlation relationships between the occupation ratios of cells and the kurtosis and variance of histograms that have been recorded in advance, and thereby calculates the occupation ratios of the cells.

By the above processing, it is possible to calculate the occupation ratio of the cells with respect to the culture medium, for each of the calculation subject regions 3d. And, by calculating the occupation ratios of the cells in the calculation subject regions 3d for the plurality of stripe images, it is possible to calculate the occupation ratio of the cells with respect to the culture medium over the entire interior of the culture vessel. Due to this, although, in the prior art, in order to calculate the occupation ratio of the cells in the culture vessel, it was necessary to obtain a phase difference image using a microscope that incorporated a phase difference optical system, and to analyze this phase difference image, and accordingly it was necessary to provide a high priced apparatus, by contrast, according to the present invention, it is not necessary to provide any high priced device such as a phase difference microscope or the like, and it is possible to calculate the occupation ratio of the cells with a cheaply priced apparatus and moreover at high accuracy.

By repeatedly executing the processing described above at predetermined time intervals, the control device 103 is able to observe the occupation ratio of the cells within the culture vessel as it changes along with time.

Figure 6:
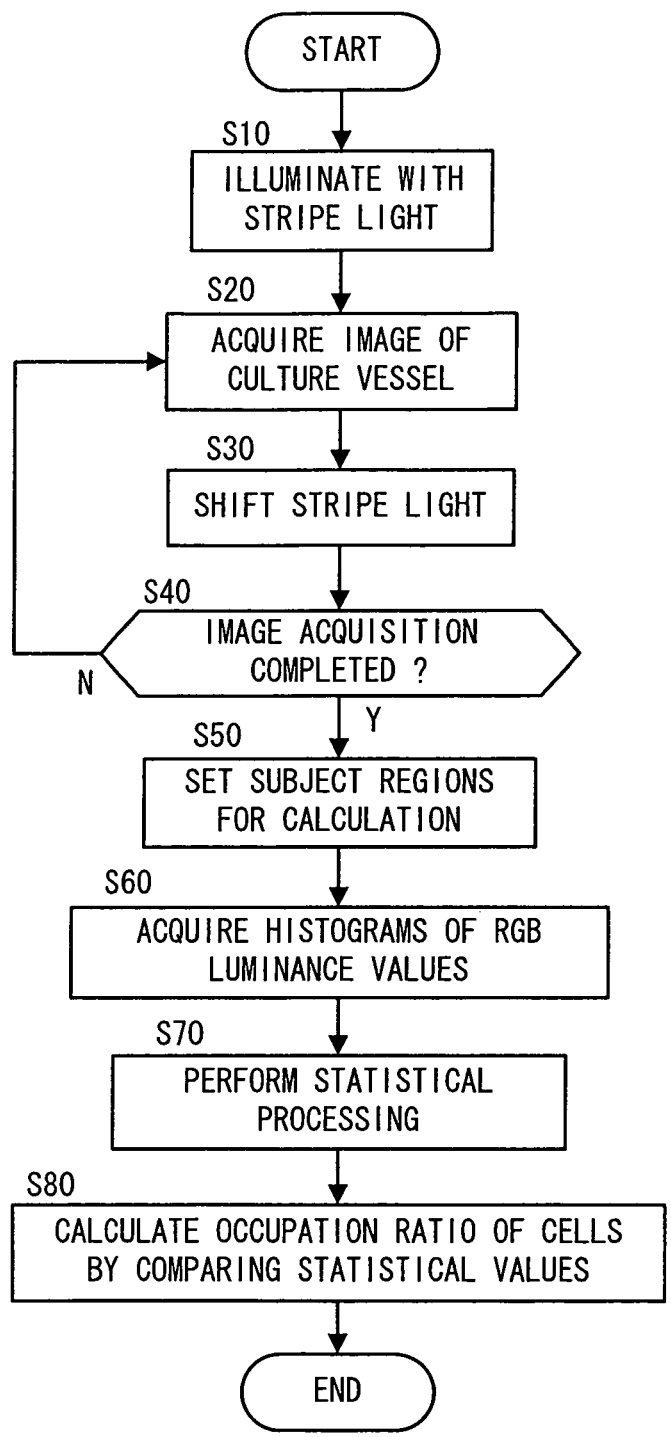
FIG. 6 is a flow chart showing processing by the observation device 100 of the first embodiment.

FIG. 6 is a flow chart showing the processing by the observation device 100 of this first embodiment. The processing shown in FIG. 6 is executed by the control device 103, and is started when a switch not shown in the figures is actuated by the user so as to issue a command for starting the calculation of the cell occupation ratio.

In a step S10, the control device 103 controls the illumination device 102 to illuminate stripe light upon the culture vessel, and then the flow of control proceeds to a step S20. In this step S20, the control device 103 controls the camera 101 to capture an image of the stripe light that has passed through the culture vessel, and records the image data that has been acquired upon the recording unit 104. Then the flow of control proceeds to a step S30.

In the step S30, the control device 103 shifts the illumination device 102 so that, as described above, the gray regions 3c in the stripe image that has been obtained at the first processing and the black regions 3b overlap, and moreover the black regions 3b in this stripe image obtained at the first processing and the black regions 3b in the newly obtained image overlap by at least width of one pixel, and thereby shifts the stripe light that is irradiating the culture vessel. Thereafter the flow of control proceeds to a step S40, in which the control device 103 makes a decision as to whether or not the illumination device 102 has been shifted by just a predetermined number of times that is set in advance, in other words as to whether or not just the acquisition has been completed of the number of stripe images that are necessary for calculating the occupation ratio of the cells.

If in the step S40 it has been decided that the acquisition of the stripe images is not completed, the flow of control returns to the step S20 and the processing sequence is repeated. On the other hand, if in the step S40 it has been decided that the acquisition of the stripe images has been completed, the flow of control proceeds to a step S50. In this step S50, the signal processing unit 103a reads in the stripe images that have been recorded upon the recording unit 104, and sets a calculation subject region 3d within the black region 3b in each stripe image, and then the flow of control proceeds to a step S60.

In the step S60, statistical processing is performed upon each of the calculation subject regions 3d so as to construct histograms of number of pixels for luminance value of each of the R, G, and B color components, and the variance and the kurtosis of each of these histograms that have been constructed are obtained. Thereafter the flow of control proceeds to a step S70, in which the signal processing unit 103a fits these values to the graphs shown in FIG. 5, which have been calculated in advance based upon experimental data and are specified the relationships between the occupation ratios of the cells and the variance and kurtosis of the histograms, and calculates the occupation ratio of the cells for each of the calculation subject regions 3d. The occupation ratio of the cells with respect to the culture medium is calculated for the entire culture vessel by executing this processing for all of the calculation subject regions 3d that are set upon the entire stripe image. Thereafter, this processing terminates.

According to the first embodiment explained above, the following beneficial operational effects may be obtained.

(1) It is arranged to irradiate the culture vessel with stripe light, to construct histograms of luminance value for the calculation subject regions 3d that have been set within the black regions 3b in the stripe images obtained by image capture with a camera at that time, and to calculate the occupation ratios of the cells within these calculation subject regions 3d based upon the variance and the kurtosis of these histograms. By doing this, while in the prior art, in order to calculate the occupation ratio of the cells in the culture vessel, it was necessary to obtain and to analyze a phase difference image using a microscope that incorporated a phase difference optical system, and accordingly it was necessary to provide a high priced apparatus, by contrast, according to the present invention, it is not necessary to provide any high priced device such as a phase difference microscope or the like, and it is possible to calculate the occupation ratio of the cells with a cheaply priced apparatus and moreover at high accuracy.

(2) It is arranged to extract only the black regions 3b from within the stripe images, and to construct the histograms of luminance value for the calculation subject regions 3d that are set in these black regions. Due to this, it is possible to calculate the occupation ratio for the cells at high accuracy by taking into account the relationship, such as shown in FIG. 5, between the kurtosis and variation of the histograms for the calculation subject regions 3d and the occupation ratio of the cells. Moreover, it is possible to reduce the processing load by limiting the range of processing of the signal processing unit 103a to the calculation subject regions 3d.

(3) If the boundary between an area that direct light strikes and an area within which light is intercepted is included within width of one pixel that makes up the image data (corresponding to four pixels upon the color CCD of FIG. 2), the pixels that correspond to this boundary are photographed as the gray zone 3c, and the problem described above occurs. However, since according to the observation device of the embodiment described above it is arranged to obtain a plurality of stripe images while shifting the illumination device 102, it is possible to eliminate these gray zones 3c and calculate the occupation ratio of the cells with high accuracy.

Embodiment Two

In the first embodiment described above, the explanation was made in terms of an example in which the occupation ratio of the cells was calculated while giving particular attention to the fact that there is a relationship as shown in FIG. 5 between the kurtosis and the variance of the histograms of luminance value for each color component in the black regions, and the occupation ratio of the cells. By contrast, in this second embodiment, an example is explained in which the occupation ratio of the cells is calculated by paying particular attention the relationship between the spatial frequency information of the image data for the culture vessel that has been obtained by irradiation of stripe light, and the occupation ratio of the cells. It should be understood that a figure like FIG. 1, a figure showing the arrangement of the color filters upon the CCD like FIG. 2, and a figure showing a concrete example of the stripe image like FIG. 3, are omitted, since they are similar to those for the first embodiment.

Figure 3:
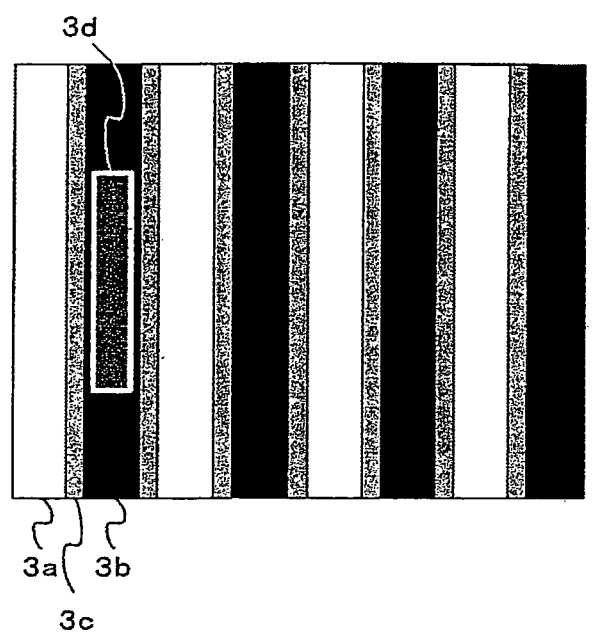
FIG. 3 is a figure showing a concrete example of a stripe image.
Figure 7:
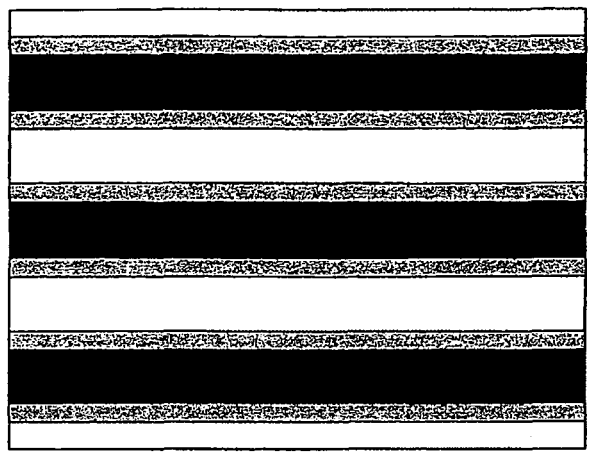
FIG. 7 is a figure showing a concrete example of a horizontal stripe image.

In this second embodiment, in a similar manner to the case with the first embodiment, the control device 103 controls the illumination device 102 and the camera 101 to obtain the stripe image shown in FIG. 3. It should be understood that, in this second embodiment, the illumination device 102 is installed so as to be able to shift the stripe light in a rotational direction. And, after having acquired a first stripe image, the control device 103 shifts the illumination device 102 so that the stripe light rotates through 90°, and thereby acquires a stripe image as shown in FIG. 7. In other words, it acquires the image shown in FIG. 3 in which stripes appear in the vertical direction (a vertical stripe image), and this image in which stripes appear in the horizontal direction (a horizontal stripe image).

Figure 8:
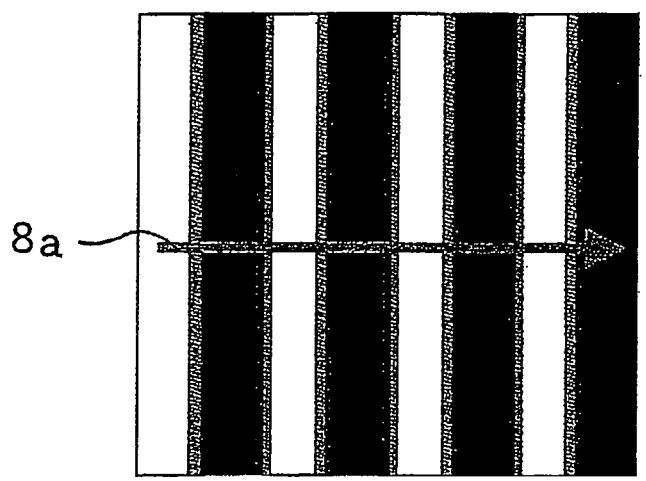
FIG. 8 is a figure showing an example of setting a calculation subject region in a second embodiment.

In the stripe images that have been acquired, the signal processing unit 103a sets calculation subject regions in the direction perpendicular to the direction of the stripes. For example, in a vertical stripe image, as shown by the arrow sign in FIG. 8, a line shaped region having a predetermined width, for example a width of three pixels, may be set as a calculation subject region 8a. And, taking this calculation subject region 8a that has been set as a subject, a line profile in the direction shown by the arrow sign of the luminance values of each of the R, G, and B color components for each pixel is acquired. By doing this, it is possible to obtain a line profile 9a for the luminance values of the R component, a line profile 9b for the luminance values of the G component, and a line profile 9c for the luminance values of the B component with the pixel positions being shown along the horizontal axis and the luminance values being shown along the vertical axis, as for example shown in FIG. 9.

Figure 9:
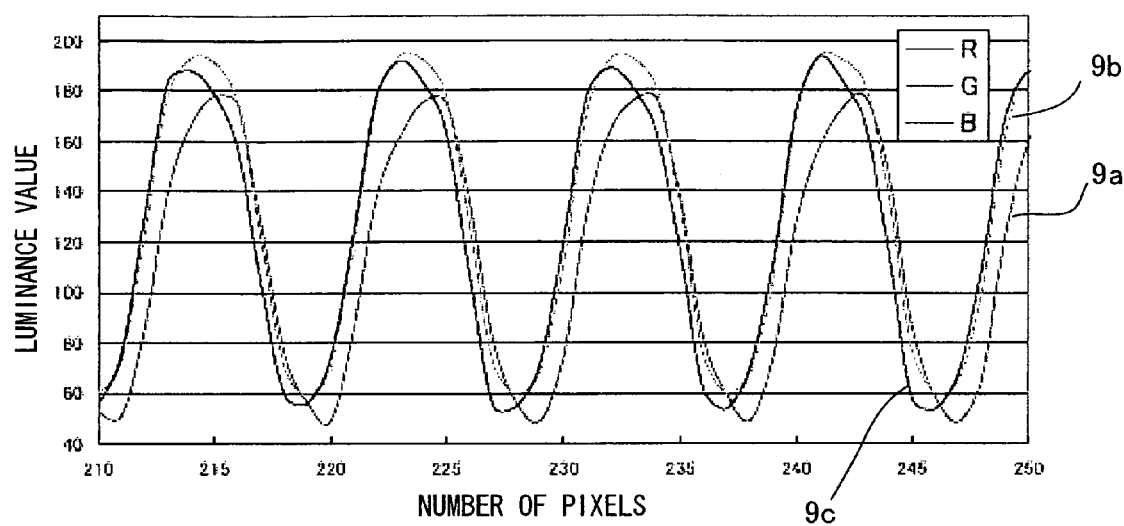
FIG. 9 is a figure showing a result of acquisition of a line profile of luminance value for each color component.

The signal processing unit 103a converts the line profiles of luminance values for each color component shown in FIG. 9 by using Fourier transform and calculates the MTF for their spatial frequencies, and calculates the occupation ratio of the cells with respect to the culture medium based upon this MTF that has been calculated. In the following, the theory by which the cell occupation ratio is calculated in this second embodiment will be explained.

Figure 10:
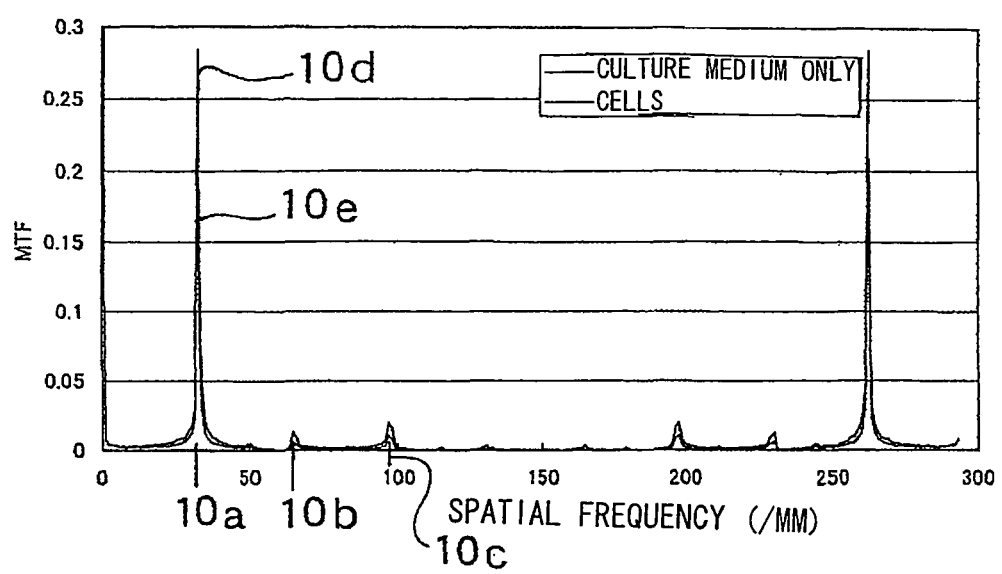
FIG. 10 is a figure showing a concrete example of a graph specifying MTF against spatial frequency.

FIG. 10 shows a graph 10d giving MTF with respect to spatial frequency for a culture medium image that has been acquired by capturing an image of only a culture medium in which no cells are present, and a graph 10e giving MTF with respect to spatial frequency for an image of a cell/culture medium that has been acquired by capturing an image of a culture medium in which cells are present. As shown in this FIG. 10, at points that are integer multiples of the basic frequency, for example at the basic frequency 10a, at a frequency 10b that is twice the basic frequency, and at a frequency 10c that is three times the basic frequency, the MTF of the cell/culture medium image is smaller than the MTF of the culture medium image.

Figures 11, 12:
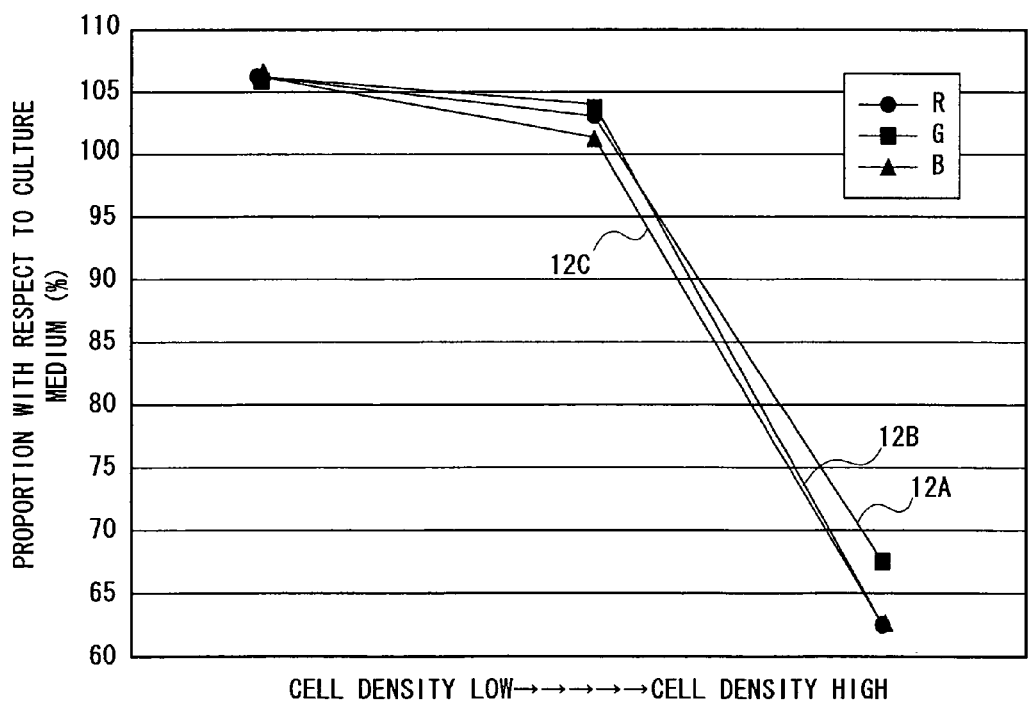
FIG. 11 is a figure showing an example of comparison of MTFs at integer multiples of a basic frequency.
FIG. 12 is a figure showing a correlation relationship, at the basic frequency, between the proportion of the MTF when cells are present with respect to the MTF when only the culture medium is present, and the occupation ratio of the cells with respect to the culture medium.

In concrete terms, as shown in FIG. 11, the MTF of the cell/culture medium image at the basic frequency 10a is 66.4% of the MTF of the culture medium image. Furthermore, the MTF of the cell/culture medium image at the frequency 10b of twice the basic frequency 10a is 48.1% of the MTF of the culture medium image. Moreover, the MTF of the cell/culture medium image at the frequency 10c of three times the basic frequency 10a is 52.6% of the MTF of the culture medium image.

Accordingly, if the correlation relationship between the proportion of the MTF of the cell/culture medium image with respect to the MTF of the culture medium image at any one of these frequencies, and the occupation ratio of the cells with respect to the culture medium, is converted to data in advance based upon experiment as shown in FIG. 12, the signal processing unit 109 can calculate the occupation ratio of the cells with respect to the culture medium based upon this data.

In the example shown in FIG. 12, the proportion (%) of the MTF of the cell/culture medium image with respect to the MTF of the culture medium image at the basic frequency is shown along the vertical axis, and the occupation ratio of the cells with respect to the culture medium is shown along the horizontal axis. And the graph 12a shows the occupation ratio of the cells and the proportion of the MTF for the R component, while the graph 12b shows the occupation ratio of the cells and the proportion of the MTF for the G component, and the graph 12c shows the occupation ratio of the cells and the proportion of the MTF for the B component.

Based upon the data shown in this FIG. 12, the signal processing unit 103a calculates the occupation ratio of the cells with respect to the culture medium in the following manner. It should be understood that although, here, the MTFs at the basic frequency is explained, it would also be possible to perform processing in a similar manner for the MTFs at integer multiples of the basic frequency.

First, the signal processing unit 103a converts the line profiles of luminance values for each color component shown in FIG. 9 by using Fourier transform and thereby calculates the MTFs for the spatial frequency. Next, using the MTF of a culture medium image that has been calculated in advance, the signal processing unit 103a calculates the proportion of the MTFs that have been calculated based upon the line profiles with respect to the MTF of the culture medium image for each color component. And, by fitting the proportions of the MTFs that have been calculated based upon the line profiles to the graphs for each color component shown in FIG. 12, it is possible to calculate the occupation ratio of the cells with respect to the culture medium within the calculation subject regions 8a for which the line profiles have been acquired.

In other words, the occupation ratio of the cells with respect to the culture medium is calculated by comparing together the proportions of the MTFs that have been calculated, and the data, recorded in advance, which specifies the correlation relationship between the proportions of the MTFs, and the occupation ratio of the cells with respect to the culture medium. It should be understood that, if some error is present in the occupation ratio that has been calculated by fitting to the graphs 12a through 12c for each color component, it would also be acceptable to arrange to calculate a representative value by averaging the occupation ratios that have been calculated for each color component; or it would also be acceptable to arrange to take the occupation ratio that has been calculated for some single color component as a representative value.

By executing the processing explained above for the entire stripe image, it is possible to calculate the occupation ratio of the cells with respect to the entire culture medium within the culture vessel. Moreover, since processing is executed both for the vertical stripe images and also for the horizontal stripe images, and the occupation ratio of the cells based upon the line profile of the stripe image in the vertical direction and also the occupation ratio of the cells based upon the line profile of the stripe image in the horizontal direction are both calculated, accordingly, if the occupation ratios of the cells in both directions are taken into account, it is possible to ascertain the occupation ratios of the cells in two dimensions.

By the control device 103 repeatedly executing the processing described above at predetermined time intervals, it is possible to observe the occupation ratio of the cells within the culture vessel as it changes with time.

Figure 13:
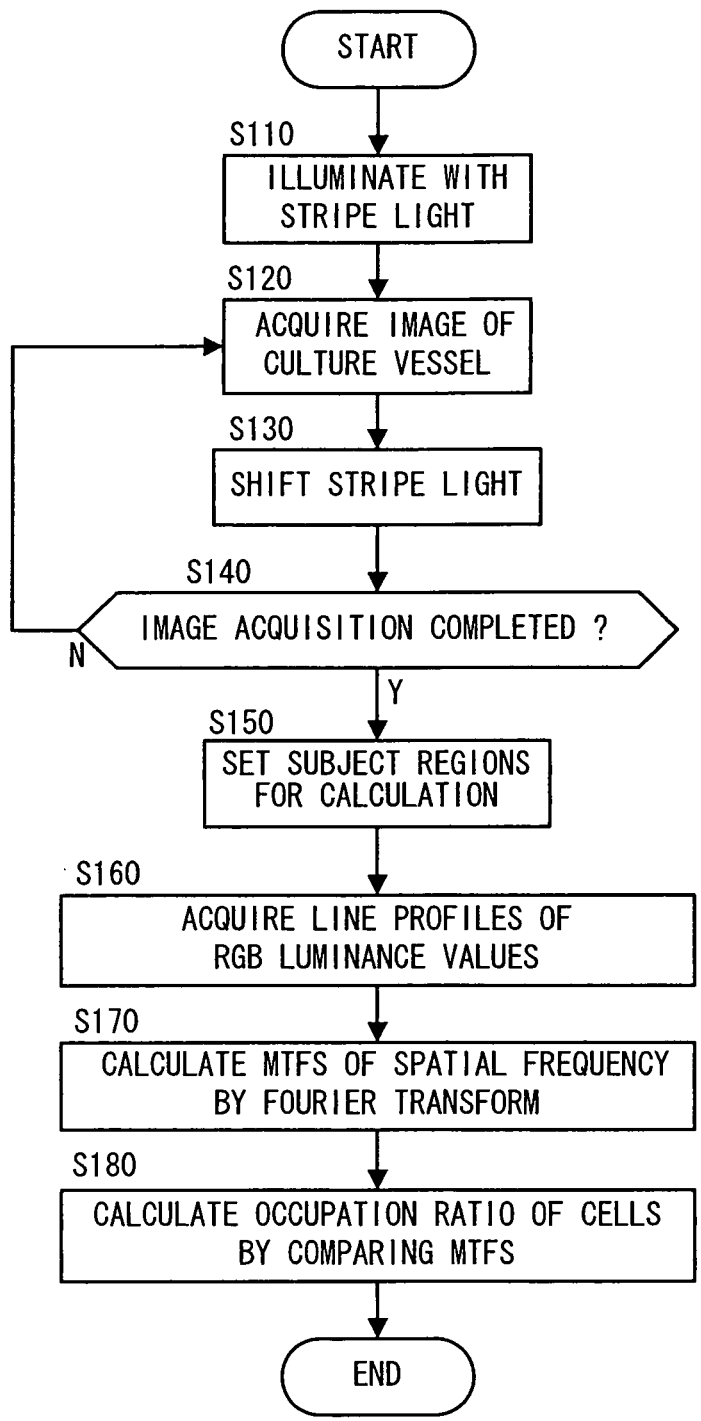
FIG. 13 is a flow chart showing processing by the observation device 100 of the second embodiment.

FIG. 13 is a flow chart showing the processing by the observation device 100 of this second embodiment. The processing shown in FIG. 13 is executed by the control device 103, and is started when a switch not shown in the figures is actuated by the user so as to issue a command for starting the calculation of the cell occupancy ratio.

In the step S110, the control device 103 controls the illumination device 102 to illuminate stripe light upon the culture vessel, and then the flow of control proceeds to a step S120. In this step S120, the control device 103 controls the camera 101 to capture an image of the light that has passed through the culture vessel, and records the image data that has been acquired upon the recording unit 104. Thereafter, the flow of control proceeds to a step S130.

In the step S130, the control device 103 shifts the illumination device 102 so as to rotate the stripe light through 90°, as described above, thus shifting the stripe light to irradiate the culture vessel. Then the flow of control proceeds to a step S140, in which the control device 103 decides whether or not the required amount of images have been acquired, in other words whether or not the acquisition of the vertical stripe images and the horizontal stripe images has been completed. If it has been decided that the acquisition of the required amount of stripe images has not been completed, then the flow of control returns to the step S120 and the above processing is repeated. On the other hand, if it has been decided that the acquisition of the required amount of stripe images has been completed, then the flow of control proceeds to a step S150.

In this step S150, for the stripe images that have been acquired, calculation subject regions 8a are set for acquiring line profiles in the directions perpendicular to the direction of the stripes. Then the flow of control proceeds to a step S160, in which, taking the calculation subject regions 8a that have been set as subjects, line profiles of luminance value are acquired for each of the R, G, and B color components of the pixels, and then the flow of control proceeds to a step S170. In this step S170, these line profiles of luminance values for each color component are converted by Fourier transform, and MTFs for spatial frequency are calculated. Then the flow of control proceeds to a step S180.

In this step S180, using the MTFs of the culture medium image that have been calculated in advance, for each color component, the ratio of the MTFs that have been calculated based upon the line profiles with respect to the MTFs of the culture medium image are calculated. And, by fitting the proportions of the MTFs that have been thus calculated to the graphs 12a through 12c for each color component shown in FIG. 12, the occupation ratio of the cells with respect to the culture medium in the regions where the line profiles in the stripe images were acquired are calculated, and, by executing this processing upon all of the stripe images, the occupation ratio of the cells in the entire culture medium within the culture vessel is calculated. Then this processing ends.

According to the second embodiment explained above, in addition to the beneficial operational effects of the first embodiment, the following beneficial operational effects may be obtained.

(1) It is arranged to calculate the occupation ratio of the cells with respect to the culture medium in the regions upon the stripe images where the line profiles were acquired, by calculating the MTFs for spatial frequency by converting the line profiles of luminance values for each color component through Fourier transform, and by fitting the results of this calculation to the graphs 12a through 12c for each color component. Due to this, it is possible to calculate the occupation ratio of the cells with respect to the culture medium at high accuracy, by taking into account the fact that, at the points that the spatial frequency is an integer multiple of the basic frequency, the MTF of the cell/culture medium decreases below the MTF of the culture medium image, and the fact that there is a mutual correlation relationship between the proportion of this decrease and the occupation ratio of the cells with respect to the culture medium.

(2) It is arranged to execute processing both upon the vertical stripe image and upon the horizontal stripe image, and to calculate an occupation ratio of the cells based upon the line profile of the stripe image in the vertical direction, and also an occupation ratio of the cells based upon the line profile of the stripe image in the horizontal direction. By doing this, it is possible to ascertain the occupation ratio of the cells two dimensionally based upon the occupation ratios of the cells in both directions.

Variant Embodiments

It should be understood that the observation devices of the embodiments described above may also be varied as described below.

(1) In the first and second embodiments described above, examples were explained in which the illumination device 102 illuminates the sample A from below, and the camera 101 captures an image of the transmitted light that has passed through the sample A from above the sample A. However, it would also be acceptable to arrange for the illumination device 102 to illuminate the sample A from above, and for the camera 101 to capture an image of the transmitted light that has passed through the sample A from below the sample A.

(2) In the second embodiment described above, it was arranged, based upon a vertical stripe image and a horizontal stripe image that have been obtained by rotating the illumination device 102 through 90°, to calculate the occupation ratio of the cells in a calculation subject region 8a that has been set in the vertical direction and also the occupation ratio of the cells in a calculation subject region 8a that has been set in the horizontal direction, and thus to be able to ascertain the occupation ratio of the cells two dimensionally. This can also be applied to the first embodiment as well; it would be acceptable to set calculation subject regions 3d within the black regions 3b for both a vertical stripe image and also a horizontal stripe image. By doing this, it is possible to calculate the occupation ratio of the cells both for the calculation subject region 3d that has been set in the vertical direction and also for the calculation subject region 3d that has been set in the horizontal direction, so that it is possible to ascertain the occupation ratio of the cells two dimensionally in the first embodiment as well.

(3) In the first and second embodiments described above, examples were explained in which the occupation ratio of the cells with respect to the culture medium in the culture vessel was calculated by the observation device 100. However, this is not to be considered as being limitative; it would also be acceptable to arrange to apply the observation device 100 of the present invention to a culture device for automatically culturing cells, and to monitor the state of the culture by calculating the occupation ratio of the cells with respect to the culture medium in the culture device. And it would be acceptable for the culture device to notify the result of performing this monitoring of the culture state to the user, or to execute passage automatically-depending to the state of the culture.

(4) While, with the first and second embodiments described above, examples were described in which the illumination device 102 was shifted in order to shift the stripe light, it would also be acceptable to arrange, by shifting the culture vessel, relatively to shift the stripe light that is irradiated upon the culture vessel.

It should be understood that the present invention is not in any way limited to the structure of the embodiments described above, provided that the characteristic function of the present invention is not lost.

What is claimed is:

1. An observation device that observes a test specimen such as cultured cells or the like, comprising:
an illumination device that illuminates the test specimen;
an image-capturing device that acquires an image of the test specimen illuminated by the illumination device;
a storage unit that stores correlation data obtained in advance, which manifests a correlation relationship between an occupation ratio of the test specimen within a culture vessel, and statistically processed data regarding to luminance information of the test specimen; and
a calculation unit that obtains the statistically processed data based upon luminance information in a specified color of the test specimen captured by the image-capturing device, and calculates the occupation ratio of the test specimen within the culture vessel using the correlation data in the storage unit.

2. The observation device according to claim 1, further comprising:
a shift unit that shifts an illumination light from the illumination device over the test specimen, wherein:
the calculation unit calculates the occupation ratio of the test specimen within the culture vessel based upon two or more images that are acquired while shifting the illumination light with the shift unit.

3. The observation device according to claim 1, wherein:
the illumination device illuminates the culture vessel with a planar light source consisting of bright portions and dark portions repeated, so that dark field regions are formed in the image acquired by the image-capturing device.

4. The observation device according to claim 3, further comprising:
a shift unit that shifts an illumination light from the illumination device over the test specimen, wherein:
the calculation unit calculates the occupation ratio of the test specimen within the culture vessel, based upon two or more images that are acquired while shifting the illumination light with the shift unit.

5. The observation device according to claim 4, wherein:
the image-capturing device comprises a plurality of pixels that each output a resolved RGB color signal having information for a plurality of colors;
a single pixel data in the image data is generated based upon the plurality of resolved RGB color signals; and
the shift unit shifts the illumination device so as to eliminate an image in a grey colored region that is formed at a boundary of a dark field region upon the image acquired by the image-capturing device, the image in the grey colored region being acquired as an image in the dark field region.

6. The observation device according to claim 3, wherein:
the calculation unit extracts an image of the dark field region from the image acquired by the image-capturing device, and calculates the occupation ratio of the test specimen within the culture vessel based upon luminance information in the specified color of the test specimen in the image in the dark field region that has been extracted.

7. The observation device according to claim 6, wherein:
the calculation unit calculates the occupation ratio of the test specimen within the culture vessel by referring to the correlation data in the storage unit while using the statistically processed data based upon luminance information in the specified color of the test specimen in the image of the dark field region.

8. The observation device according to claim 1, wherein:
the statistically processed data is a variance and a kurtosis of a histogram that is generated based upon the luminance information in the specified color.

9. An observation device that observes a test specimen such as cultured cells or the like, comprising:
an illumination device that illuminates the test specimen;
an image-capturing device that acquires an image of the test specimen illuminated by the illumination device;
a storage unit that stores correlation data obtained in advance, which manifests correlation relationship between an occupation ratio of the test specimen within a culture vessel and statistically processed data of spatial frequency information of the test specimen; and
a calculation unit that obtains the statistically processed data based upon the spatial frequency information of the test specimen captured by the image-capturing device, and calculates the occupation ratio of the test specimen within the culture vessel using the correlation data in the storage unit.

10. The observation device according to claim 9, further comprising:
a shift unit that shifts an illumination light from the illumination device over the test specimen in a rotational direction, wherein:
the calculation unit calculates the occupation ratio of the test specimen within the culture vessel based upon two or more images that are acquired while shifting the illumination light with the shift unit.

11. An observation device that observes a test specimen such as cultured cells or the like, comprising:
an illumination device that illuminates the test specimen;
an image-capturing device that acquires an image of the test specimen illuminated by the illumination device;
a storage unit that stores correlation data manifesting a correlation relationship between an occupation ratio of the test specimen within a culture vessel and statistically processed data of spatial frequency information of the test specimen; and
a calculation unit that obtains the statistically processed data based upon the spatial frequency information of the test specimen captured by the image-capturing device, and calculates the occupation ratio of the test specimen within the culture vessel using the correlation data in the storage unit, wherein:
the calculation unit calculates the spatial frequency information from luminance information in a specific color of the test specimen in the image acquired via image capture by the image-capturing device.

12. The observation device according to claim 9, wherein:
the statistically processed data of the spatial frequency information is a proportion of the spatial frequency information of an image when the test specimen is occupying the interior of the culture vessel, with respect to the spatial frequency information of an image when no test specimen is occupying the interior of the culture vessel.

* * * * *